United States Patent [19]

Leaf et al.

[11] Patent Number: 5,082,831

[45] Date of Patent: Jan. 21, 1992

[54] TOTAL BODY WASHOUT SOLUTION AND METHOD OF USE

[75] Inventors: Jerry D. Leaf, Downey; Michael G. Federowicz, Riverside, both of Calif.

[73] Assignee: Cryovita Laboratories, Inc., Riverside, Calif.

[21] Appl. No.: 446,006

[22] Filed: Dec. 5, 1989

[51] Int. Cl.$^5$ .................. A61K 37/26; A61K 31/715; A01N 1/02

[52] U.S. Cl. ........................... 514/56; 514/60; 514/832; 514/833; 435/1; 128/400; 128/401; 604/4

[58] Field of Search .................. 514/56, 60, 832, 833; 604/4; 128/400, 401; 435/1

[56] References Cited

U.S. PATENT DOCUMENTS

| | | | |
|---|---|---|---|
| 3,523,938 | 8/1970 | Hershenson et al. | 536/111 |
| 4,798,824 | 1/1989 | Belzer et al. | 435/1 |
| 4,873,230 | 10/1989 | Belzer et al. | 514/60 |
| 4,879,283 | 11/1989 | Belzer et al. | 514/60 |
| 4,920,044 | 4/1990 | Bretan | 435/1 |
| 4,923,442 | 5/1990 | Segall et al. | 514/23 |

FOREIGN PATENT DOCUMENTS 3030863 3/1982 Fed. Rep. of Germany.

Primary Examiner—Ronald W. Griffin
Attorney, Agent, or Firm—Benman & Collins

[57] ABSTRACT

The present invention is concerned with improved aqueous asanguineous perfusates, blood substitutes for profound hypothermia, and method of using the same. The perfusates comprise:

| Component | Molar Conc., mM | Grams/liter |
|---|---|---|
| Hydroxyethyl starch, MW = 500,000 | 40 to 60 gms | |
| Glucose | 5–15 | 0.9–2.7 |
| Sodium bicarbonate | 5–20 | 0.42–1.68 |
| Potassium chloride | 15–40 | 1.15–3.33 |
| Calcium chloride | 0.5–2.04 | 0.074–0.294 |
| Magnesium chloride | 0.25–2.5 | 0.051–0.510 |
| HEPES or THAM | 7.2–15 | 1.72–3.90 |
| Sodium phosphate, monobasic, MW = 120.0 | 7.2–15 | |
| Mannitol or sucrose | 0–170 | 0–30.97. |

5 Claims, 2 Drawing Sheets

TOTAL BODY WASHOUT SOLUTION AND METHOD OF USE

TECHNICAL FIELD

This invention is concerned with an improved for use in deep hypothermia with asanguineous perfusion. It is also concerned with a method of using the solution.

BACKGROUND ART

Some time ago, physiologists determined that cellular metabolism proceeds at reduced rates as the temperature is lowered. The general reduction in metabolic energy requirements is expressed in the so-called Q-10 rule, i.e., for each 10° C. of reduced temperature, the metabolic rate is diminished by 50%. With normal human body temperature being 37° C., at 27° C. the metabolic requirements are reduced to 50%; at 17° C. they are 25% of normal; and at 7° C. they are 12.5% of normal. Medical applications of hypothermia prior to the advent of heart-lung machines were restricted due to the fibrillation temperature of the human heart, i.e., 28° C.

In 1957, the first clinical open heart procedure using a heart-lung machine was accomplished. The ability to oxygenate blood, mechanically maintain the circulation, and control temperature in extracorporeal devices provided a means to achieve deep hypothermia below the fibrillation temperature of the human heart. Complex open heart repairs made possible by heart-lung machines require extended time periods and non-beating, arrested hearts. These procedures are done more safely using hypothermia, for example, 22° to 28° C.

Repair of cardiac anomalies in pediatric patients require total circulatory arrest of periods of 45 to 120 minutes, which can only be done in deep hypothermia, i.e., 15° to 17° C. Human hypothermia with circulating blood presented problems. Red cell membranes become rigid, and exhibit sludging, rouleau formation, and cold agglutination during hypothermia. This can inhibit capillary blood flow, resulting in regional ischemia and tissue injury. Hemodilution with electrolyte solutions helped but did not eliminate these problems. Lower temperatures for greater protection of patients require bloodless perfusion.

As early as 1969, there were experiments with patients in stage 4 hepatic coma that required the use of asanguineous perfusion. This involved total body washout (TBW) of the patients' blood using hypothermia followed by complete blood replacement. Few patients survived. Dog experiments to improve the electrolyte solutions used in these procedures showed some advances, but not enough to justify widespread clinical application.

In 1978, the present inventor began experiments using canine models for TBW to test blood replacement solutions. Canine models provided an opportunity to test the response of all organs systems to new solutions. These experiments were designed to demonstrate the feasibility of profound hypothermia, i.e., 5° to 7° C. in intact mammals. They were also used to develop solutions that could be used for organ preservation at sub-zero temperatures.

Early experiments employed phosphate buffered electrolyte solutions using polyvinylpyrrolidone (PVP) or dextran 40 as colloids. The principal cause of death in animals with total blood washout was pulmonary edema. Dextran 40 solutions persisted in producing edema, particularly in the pancreas and the lungs. Plasma protein as a colloid showed the same results as dextran 40. PVP was abandoned when acute lesions in the liver were discovered during the course of perfusion.

Varied electrolyte and buffer combinations were tried without success.

DISCLOSURE OF INVENTION

I have discovered a procedure and a perfusate which gives superior results in total blood washout in deep hypothermia with asanguineous perfusion. The solution consists essentially of the following:

| Component | Molar Conc., mM | Grams/Liter |
|---|---|---|
| Hydroxyethyl starch MW = 500,000 | 40 to 60 gms | |
| Glucose | 5–15 | 0.9–2.7 |
| Sodium bicarbonate | 5–20 | 0.42–1.68 |
| Potassium chloride | 15–40 | 1.15–3.33 |
| CaCl$_2$.6H$_2$O | 0.5–2.04 | 0.074–0.294 |
| MgCl$_2$.6H$_2$O | 0.25–2.5 | 0.051–0.51 |
| HEPES* | 7.2–15 | 1.72–3.90 |
| Sodium phosphate, monobasic, MW = 120.0 | 7.2–15 | |
| THAM** | 15–27 | |
| Mannitol | 0–170 | 0–30.97 |

*N-2-hydroxyethylpiperazine-n'-2-ethanesulfonic acid, MW = 260.3
**2-amino-2(hydroxymethyl)-1,3-propanediol, MW = 121.1

Sucrose may replace mannitol on a direct mole for mole basis, up to 170 mMol. Mixtures of mannitol and sucrose can also be used. The range of sucrose is 0 to 170 mMol, to 58.19 gms/liter, depending on the amount of mannitol used.

Glutathione (free acid; MW=307.33) may also be used. The useful range is 3 to 5 mMol, 0.92 to 1.54 grams/liter. Its antioxidant properties are of particular importance if mannitol is not used in the TBW solution.

The osmolality of the solution is 388 to 403 mOsm; and the pH is adjusted to about 8.0 to 8.2 by sodium hydroxide. 1,000 IU of heparin is added per liter of solution, and water for injection (U.S.P.) is also added to final volume.

BEST MODES FOR CARRYING OUT THE INVENTION

Figure 1:
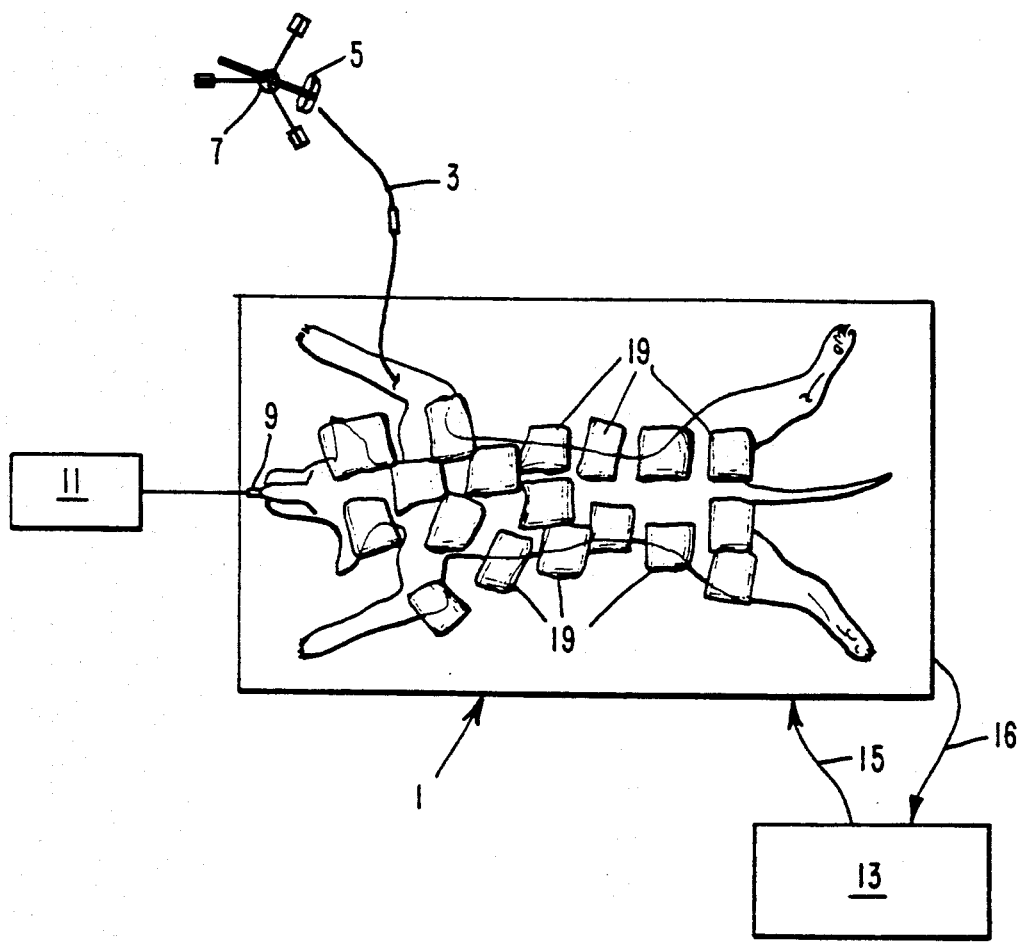
FIG. 1 is a schematic view of a preferred arrangement of equipment to be used in the surface cooling, respiration and medication of an animal.

The use and effectiveness of this invention is best illustrated by the following experiment. Six predominantly mongrel dogs of both sexes, each weighing from 22 to 27 kg, were used. The experiment will now be described with one dog as representative.

The dog was placed on cooling blanket 1 and premedicated with 50 mg of chlorpromazine and anesthetized with 30 mg/kg of sodium pentobarbital (Nembutal) administered intravenously through an 18 ga. Angiocath (not shown) placed in a front leg. The chlorpromazine and Nembutal were administered through I.V. line 3 which was connected at the other end to medication bag or bottle 5. Bag or bottle 5 was suspended, in conventional fashion, from I.V. pole 7.

Immediately following anesthetization, the animal was intubated with cuffed endotracheal tube 9. Ventilation through tube 9 was begun with a Harvard Instruments Dual Phase Control Respirator 11, using room air and an inspiration to expiration ratio of 1:1.

The temperature of blanket 1 was adjusted by circulating water from heater-cooler 13 through line 15 and return through line 17. The dog on blanket 1 was packed in bags 19 of crushed ice. Rectal and esophageal temperatures were measured to the nearest 0.2° C., using a thermocouple meter (not shown), such as a YSI model 46TUC. EKG was monitored on an Electrodyn model CB121B system (not shown).

The respirator was adjusted to deliver a tidal volume of 450 cc at a rate of 22 respirations per minute throughout induction of hypothermia and during rewarming. At fifteen minute intervals during induction of hypothermia and rewarming, the animals were given intermittent deep sigh ventilations to maintain good lung expansion and guard against atelectasis.

A particularly preferred asanguineous formulation (I) was used in this experiment. It consists essentially of the following:

| Component | Molar Conc., mM | Grams/Liter |
| --- | --- | --- |
| Hydroxyethyl starch MW = 500,000 | 55 | |
| Glucose | 10.0 | 1.8 |
| Sodium bicarbonate | 10.0 | 0.84 |
| Potassium chloride | 28.3 | 2.11 |
| Calcium chloride | 1.0 | 0.11 |
| Magnesium chloride | 1.0 | 0.095 |
| HEPES | 7.2 | 1.72 |
| Mannitol | 170 | 30.97 |

Heparin was added at the rate of 1,000 IU per liter and the pH was adjusted to 8.0 to 8.2. Water for injection (U.S.P.) was also added to make the desired volume. The osmolality was 388 to 403 mOsm.

During asanguineous perfusion, the inspiration to expiration ratio was changed to 2:1 and the rate of respirations was slowed to seven per minute. Three to five sigh ventilations were given every thirty to forty minutes during asanguineous perfusion. After the start of asanguineous perfusion and at irregular intervals thereafter, the patency of the endotracheal tube cuff seal in the trachea was evaluated by auscultation; this was done to guard against loss of seal patency secondary to temperature induced contraction of gas in the tube cuff.

At the beginning of external cooling, administration of pre-washout medications was begun via peripheral IV line 3 connected to a front leg Angiocath. A drip of 5% sodium bicarbonate was begun to maintain appropriate pH during induction of hypothermia. The pH of mammals is usually kept at what is normal for them at normothermia, even when they are exposed to hypothermia. This is inappropriate. The pH of blood or perfusate changes with temperature. For each degree Centigrade, the blood temperature is lowered, pH increases by 0.0147 pH units. This quantity, 0.0147, is called the Rosenthal factor.

The pH that is appropriate is in the range seen in poikilotherm animals. As a practical example, a man's normal temperature is 37° C. and his pH is 7.4. If the body temperature is reduced to 5° C., his appropriate pH should be at least 7.9. The general requirement for respiration in the context of hypothermia is that respiration be aggressively used to lower $CO_2$ in order to maintain high blood/perfusate pH. Pharmaceutical buffering agents given intraveinously are only given to increase pH after $CO_2$ has been lowered. This approach reduces the amount of buffer required.

Other medications were then administered through I.V. line 3 in the following order:

| Drug | Dosage | Range |
| --- | --- | --- |
| Cimetidine* | 4.17 | 4.0 to 12.0 |
| Metubine Iodine* | 0.2 | 0.2 to 0.4 |
| Atropine** | 0.4 | 0.2 to 0.5 |
| Verapamil* | 0.15 | 0.1 to 0.2 |
| Solu-Medrol* | 30.04 | 10.0 to 40.0 |
| Mannitol*** | 2 | 1 to 3 |
| Erythromycin* | 15 | 15.0 to 30.0 |
| Heparin* | 420 | 400 to 500 |

*mg/kg
**total dose
***g/kg 50 cc Maalox was administered via gastric tube (not shown).

Atropine was given to reduce mucus secretion and against the possibility of bradycardia secondary to the administration of Verapamil. Cimetidine and aluminum hydroxide (Maalox) were administered to inhibit the secretion of gastric acid and neutralize the acidity of the stomach contents; this reduces the risk of gastric ulceration which is a known sequelae of deep hypothermia in mammals. Metubine iodine was used to inhibit shivering during induction of hypothermia. Verapamil controls calcium influx which may result from reduced ion pumping secondary to profound hypothermia.

Erythromycin is the antibiotic of choice because it is the only one known to the present inventor that does not increase cold agglutination of blood.

When ice packs 19 were applied to begin surface cooling, the femoral areas were shaved and then prepped with betadine solution. The areas were then draped with sterile towels and fenestrated drapes. The sterile field was extended over the upper body with a 45"×77" disposable drape sheet.

Bilateral femoral cutdowns were performed, opening the skin with a #10 scalpel blade and maintaining hemostasis with an electrocautery. The right and left femoral arteries and veins were dissected free. Heparin was administered prior to cannulation and extracorporeal circulation. The right and left femoral arteries and veins were ligated distally with #1 silk.

A venous return cannula 21, USCI type 1.967, size 20 or 22 French, depending on vessel size, was introduced through a venotomy in the right femoral vein. It was advanced until the tip was near the right heart, and then it was secured with a #1 silk tie.

A second venous cannula 23, USCI type 1967, 20 Fr., was introduced into the left femoral vein and secured with a #1 tie.

A stainless steel perfusion cannula 25 was placed in the right femoral artery through an arteriotomy made with a #11 scalpel blade and secured with a #1 silk tie.

Central venous pressure (CVP) was monitored by a 24"×17 ga. Intracath introduced through an equal Y-connector 27 with Leur port in venous return line 29 and advanced beyond the tip of venous cannula 23. When the pulmonary artery pressure (PA) was monitored, a Swan-Ganz catheter was introduced instead of an Intracath.

A Sherwood arterial pressure monitoring catheter was introduced through an arteriotomy in the left femoral artery and secured with a 3-0 silk tie. CVP or PA and arterial pressure catheters were connected to Statham P23dB transducers for pressure measurements which were then recorded on a Hewlett-Packard model 7700 recorder. The venous cannulas were connected to the extracorporeal circuit venous return line 29 with a Cobe Labs ⅜" equal Y-connector 27, and the arterial cannula 25 was connected to the ¼" arterial perfusion line 31.

The extracorporeal circuit for perfusion and rewarming consisted of an arterial roller pump 33, a Shiley S-70 bubble oxygenator 35, a Sarns Torpedo heat exchanger 37, a Pall EC1440 40 micron blood filter 39 and two Travenol Modulung reservoir bags 41, which were used for blood collection during washout and asanguineous perfusion. All tubing was Tygon S50HL. Arterial temperature was monitored via thermistor probes, using a Shiley Labs temperature monitor (not shown).

A perfusate delivery system consisting of an ice-cooled perfusate reservoir 43, a roller pump 45, and a Pall PP3802 0.2 micron filter 47 was used to sterilize and deliver perfusate to oxygenator 35. Carbon dioxide and/or oxygen are delivered to oxygenator 35 from oxygen tank 65 (100% oxygen) and carbon dioxide tank 67 (5% carbon dioxide) through line 69 and gas filter 71.

A dialysis circuit consisted of a standard hemodialysis loop employing an Erika HPF-200 dialyzer 48 (hollow fiber kidney) and a Travenol recirculating single pass "batch type" hemodialysis machine 49 (with negative pressure dialysis capability). Blood from arterial line 31 can be directed to dialyzer 48 through roller pump 51 and returned to venous line 29 through line 53. Hemodialysis is carried out during rewarming; the rest of the time this circuit is closed off by standard means, such as a valve.

Dialysis during blood perfusion and rewarming is desirable. It can normalize blood electrolytes, allow minimal blood replacement, hemoconcentrate, remove metabolic waste products and control pH during rewarming.

The perfusion circuit was formed by separating venous line 29 and arterial line 31 from their respective cannulae and joining them together. The circuit was then primed by pouring into oxygenator 35 through an inlet port a solution of 250 cc of Hespan 6% hydroxyethyl starch in normal saline, 23 mEq of sodium bicarbonate (25 cc), and 1,000 cc of blood which was preserved with citrate-phosphate-dextrose with adenine. The blood was collected no more than 12 hours before the start of partial bypass. Each 500 cc of preserved blood was converted prior to use by the addition of 2,500 units of sodium heparin and 5 cc of 10% calcium chloride. Total priming volume was 1,250 cc. The prime was recirculated and cooled to 15° C. by passing through heat exchanger 37 prior to the start of partial bypass.

The superiority of perfusates and preservative flush solutions in which the ionic content is adjusted to mimic the intracellular rather than the extracellular environment has been previously documented. For this reason, an intracellular perfusate solution of formula I above was made. This solution was hypocalcemic, to reduce the possibility of calcium influx during hypothermia. It was employed for both washout and asanguineous recirculation.

Previous, unpublished work in our laboratory had documented problems with severe acidosis. Consequently, a decision was made to replace most of the glucose in the earlier solutions with mannitol; it seemed that too much glucose may drive anaerobic metabolism during deep hypothermia. However, sucrose can be used instead of mannitol.

The phosphate buffer previously used was replaced with HEPES because it was known that a HEPES buffered gluconate based perfusate provided excellent three day preservation of canine kidneys. Another useful buffer is THAM; it may be used alone or in combination with sodium phosphate.

Six liters of perfusate were prepared the day before each experiment by weighing out reagent or drug grade powdered ingredients and dissolving them in USP water for injection. Calcium chloride and magnesium chloride were added last, and the pH of the solution was adjusted to 8.2 to 8.4 with sodium hydroxide. Unfiltered perfusate was stored overnight on crushed ice. Immediately prior to use, the perfusate was sterilized by passage through a 0.2 micron filter.

Partial femoral-femoral bypass was begun at rectal temperatures between 28° C. and 32° C. Ventricular fibrillation occurred at temperatures as high as 27° C. and as low as 15° C. Initial blood flow rates of 1 to 1.5 liters per minute were employed and sanguineous perfusion was continued until rectal temperatures of 10° C. to 12° C. were achieved. Blood temperature and subsequently perfusate temperature can be lowered or raised by passing the fluid through roller pump 33 to heat exchanger 37. The temperature in heat exchanger 37 is adjusted by the flow of water from heater-cooler 57 through line 59 and back through line 55.

When rectal temperature of 10° to 12° C. was achieved, perfusion was discontinued and the animals exsanguinated through line 29 into the reservoir of oxygenator 35. The contents of oxygenator 35 were then drained into Modulung reservoir bags 41 through line 42, which had means (not shown) for isolating bags 41 from oxygenator 35. Line 42 was flexible so that bags 41 can be raised to allow blood to flow back into oxygenator 35 for the rewarming phase.

Oxygenator 35 was charged with one liter of TBW solution from perfusate reservoir 43, and this was perfused open circuit through the animals. Four additional one liter open circuit flushes were employed before charging the oxygenator with one liter of perfusate and closing the circuit for extended asanguineous perfusion. Arterial perfusion pressure was kept between 25 to 50 mm Hg. These flushes, which removed residual blood from the animal's vascular system, were removed from circulation through line 61 into dump reservoir or drainage 63. Line 61 was then isolated from line 29.

Figure 2:
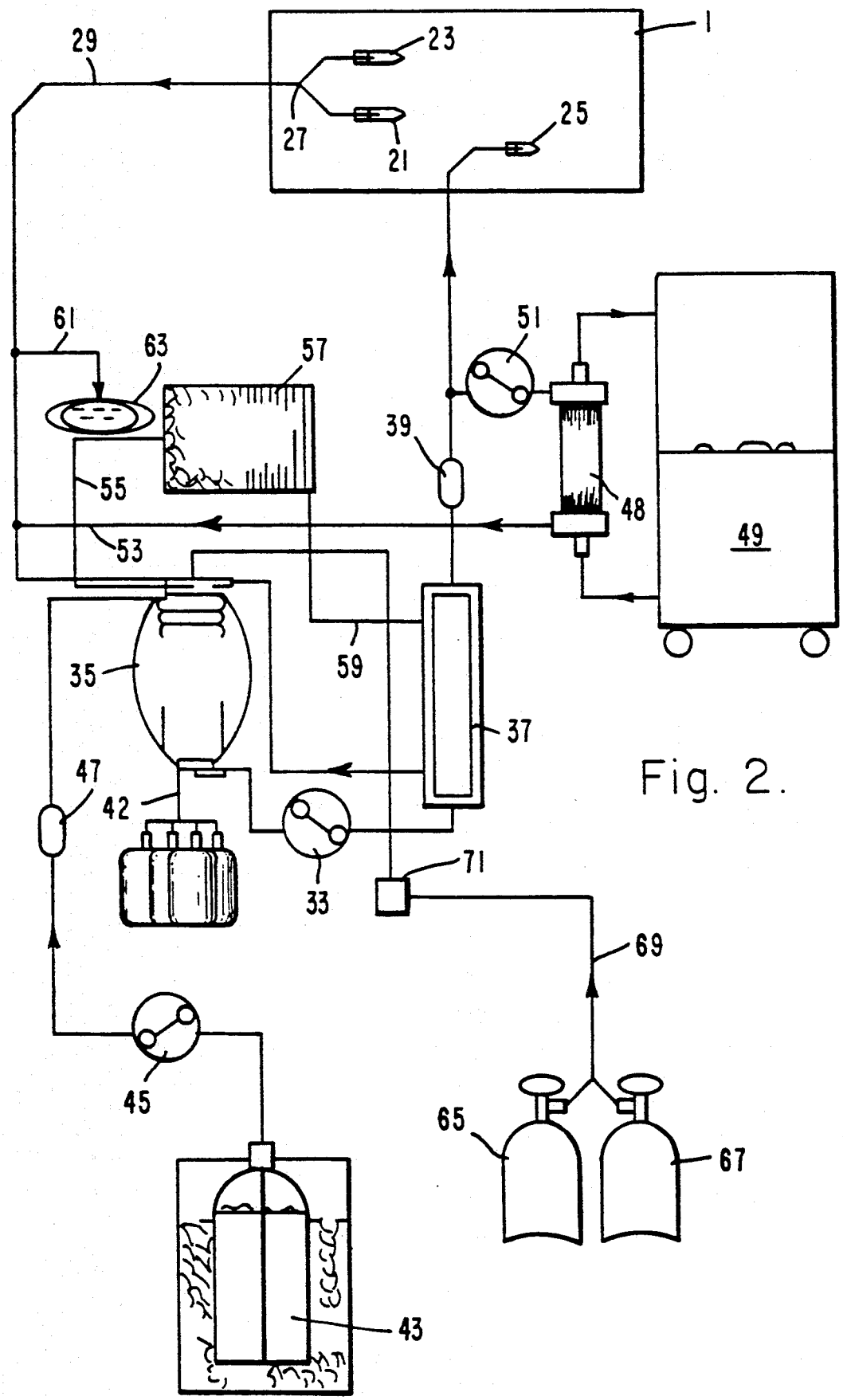
FIG. 2 is a schematic view of a preferred apparatus to be used in administering the novel solutions of this invention.

Esophageal temperature was reduced to approximately 32° C. with surface cooling, while surgery and preparation for bypass was completed. Perfusion cooling with a heart lung machine (FIG. 2) was then used to bring the temperature to 10° C. before exsanguination. Asanguineous perfusion was then used to achieve a stable temperature of 4° to 6° C. for the TBW period, which lasted approximately 4 hours total. During rewarming perfusion, body temperature was raised to 10° to 15° C. by passing perfusate through heat exchanger 37 before blood was reintroduced into the animal through line 31.

Hematocrit determinations to evaluate the extent of blood washout were carried out at least one hour after the start of asanguineous recirculation. During TBW, hematocrit was 0.5%. At fifteen to thirty minute intervals throughout perfusion, arterial blood samples were obtained and tested for pH, $pO_2$ and $pCO_2$. Blood samples were taken through the entire procedure for analysis of SGOT, alkaline phosphate, BUN, creatinine, total protein, total bilirubin, phosphorus, glucose, amylase, lipase, CPK, LDH, sodium, potassium, calcium, and chloride.

All six dogs used in the experiment survived. No other asanguineous whole body perfusion solution has demonstrated this survival rate under similar conditions. Adequate oxygenation and pH control are possible with a solution of this invention. Laboratory analysis of enzyme markers of tissue injury showed elevated SGOT and SGPT; however, the experiment used ligated hind limb vasculature and the effected muscle is an anticipated source of these enzymes. Even so, post-operative data shows return to normal enzyme levels with corresponding normal function of the hind legs. In addition, amylase was elevated but returned to normal post-operatively, indicating normal pancreatic function.

One dog was sacrificed three weeks post-operatively for organ pathology studies. All organs showed normal morphology by microscopy, except the liver, which was only remarkable for its lack of normal glycogen stores. Glycogen depletion was probably due to the nutritional state of the dog at the time of sacrifice. Gross examination revealed no organ pathology.

Post-operative X-ray chest films showed clear lungs and normal cardiovascular pictures. There was reduced in testinal mobility for a few days. Pre- and post-operative behavior patterns persisted in individual animals, though two animals had seizures that were controllable by dilantin; the use of post-operative amino acids to supplement nutrition may have been a causative factor.

The only damage that persisted was hearing acuity in one animal, due to extended use of antibiotic. Wound infections in two animals were resolved by antibiotic therapy. No known long term adverse effect was evidenced in any of the experimental animals. Similar canine research in the past had a survival rate of 30 to 50%.

INDUSTRIAL APPLICATION

The novel formulations and procedures of this invention will permit extended periods of circulatory arrest in pediatric open heart surgery and in adult patients, such as aortic aneurysm repair, enhancing outcome in terms of improved morbidity and mortality. Some types of brain surgery have shown a need for profound hypothermia, which can only be satisfied by TBW techniques.

The transport of organ donors in profound hypothermia and the harvesting of multiple organs for transplanting is also possible using TBW, with reduced ischemic injury to the harvested organs. In addition, removal of toxic substances from circulating blood, or treatment of carbon monoxide poisoning, is possible by TBW and blood replacement. The use of this TBW procedure in the treatment of inoperable tumors with chemotherapy is also possible.

I claim:

1. An aqueous perfusate composition comprising:

| Component | Molar Conc., mM | Grams/Liter |
|---|---|---|
| Hydroxyethyl starch, MW = 500,000 | | 40 to 60 gms |
| Glucose | 5–15 | 0.9–2.7 |
| Sodium bicarbonate | 5–20 | 0.42–1.68 |
| Potassium chloride | 15–40 | 1.15–3.33 |
| Calcium chloride | 0.5–2.04 | 0.074–0.294 |
| Magnesium chloride | 0.25–2.5 | 0.051–0.51 |
| HEPES or THAM | 7.2–15 | 1.72–3.90 |
| Sodium phosphate, monobasic, MW = 120.0 | 7.2–15 | |
| Mannitol or sucrose | 0–170 | 0–30.97 | and an effective amount of heparin to prevent coagulation.

2. A perfusate composition of claim 1 containing about 1,000 IU heparin per liter.

3. A perfusate composition of claim 1, the pH of which has been adjusted to about 8.0 to about 8.2.

4. A perfusate composition of claim 1 which contains 3 to 5 mM glutathione.

5. A perfusate composition consisting essentially of the following:

| Component | mMols | Gms/liter |
|---|---|---|
| Hydroxyethyl starch, MW = 500,000 | | 55 gms |
| Glucose | 10.0 | 1.8 |
| Sodium bicarbonate | 10.0 | 0.84 |
| Potassium chloride | 28.34 | 2.11 |
| Calcium chloride | 1.0 | 0.11 |
| Magnesium chloride | 1.0 | 0.095 |
| HEPES or THAM | 7.2 | 1.72 |
| Mannitol | 170 | 30.97 |

\* \* \* \* \*